US009383729B2

(12) United States Patent
Allgeuer et al.

(10) Patent No.: US 9,383,729 B2
(45) Date of Patent: Jul. 5, 2016

(54) LINKING ON-LINE ANALYSIS AND TRACER TECHNOLOGY

(75) Inventors: Thomas T. Allgeuer, Wollerau (CH); Enric Comas, Tarragona (ES)

(73) Assignee: Dow Global Technologies LLC, Midland, MI (US)

( * ) Notice: Subject to any disclaimer, the term of this patent is extended or adjusted under 35 U.S.C. 154(b) by 459 days.

(21) Appl. No.: 13/825,282

(22) PCT Filed: Sep. 20, 2011

(86) PCT No.: PCT/US2011/052351
§ 371 (c)(1),
(2), (4) Date: Aug. 21, 2013

(87) PCT Pub. No.: WO2012/040203
PCT Pub. Date: Mar. 29, 2012

(65) Prior Publication Data
US 2013/0326852 A1    Dec. 12, 2013

(30) Foreign Application Priority Data

Sep. 21, 2010   (EP) .................................... 10382253

(51) Int. Cl.
| G01N 21/85 | (2006.01) |
| G05B 1/01 | (2006.01) |
| G01N 21/31 | (2006.01) |
| G01N 21/64 | (2006.01) |

(52) U.S. Cl.
CPC *G05B 1/01* (2013.01); *G01N 21/31* (2013.01); *G01N 21/85* (2013.01); *G01N 2021/6417* (2013.01); *G01N 2021/6439* (2013.01); *G01N 2021/8592* (2013.01); *Y10T 29/49771* (2015.01)

(58) Field of Classification Search
CPC .......... G05B 1/01; G05B 21/85; G05B 21/31; G05B 2021/6439; G05B 2021/6417; G05B 2021/8592; G05B 33/442; Y10T 29/49771
See application file for complete search history.

(56) References Cited

U.S. PATENT DOCUMENTS

| 6,297,508 | B1 | 10/2001 | Barmore et al. |
| 7,230,113 | B2 | 6/2007 | Chauhan et al. |
| 7,674,532 | B2 | 3/2010 | Einhorn et al. |
| 2003/0112423 | A1 * | 6/2003 | Vig ........................ G06K 5/00 356/71 |
| 2005/0277710 | A1 * | 12/2005 | Joyce ................... G01N 33/442 523/210 |
| 2006/0106621 | A1 * | 5/2006 | Kushida ................. C09K 11/77 235/468 |
| 2008/0025594 | A1 * | 1/2008 | Metzger .................. G07F 7/086 382/141 |
| 2008/0231851 | A1 | 9/2008 | Pan et al. |
| 2010/0056688 | A1 | 3/2010 | Greer et al. |
| 2010/0057649 | A1 | 3/2010 | Lee et al. |
| 2010/0140550 | A1 | 6/2010 | Keller et al. |
| 2011/0089241 | A1 | 4/2011 | Medintz et al. |

FOREIGN PATENT DOCUMENTS

| JP | 2001-329588 | 11/2001 |
| JP | 2001329588 A | 11/2001 |
| JP | 2003039808 A | 2/2003 |
| WO | 2005055236 A1 | 6/2005 |

OTHER PUBLICATIONS

International Prelimiinary Report on Patentability for PCT/US2011/052351, Issue Date Mar. 26, 2013, 6 pages.
PCT/US2011/052351, International Search Report and Written Opinion.
EP 10 382 253.2 European Search Report and Written Opinion.
EP 10 382 253.2, Response Written Opinion.

\* cited by examiner

*Primary Examiner* — David Bryant
*Assistant Examiner* — Ruth G Hidalgo-Hernande

(57) ABSTRACT

The present invention relates to a method of obtaining value from providing fabrication equipment comprising the following steps. Fabrication equipment is provided to an article producer, which equipment includes an on-line analyzer for detecting the presence of a tracer element. Raw material which contains the proprietary tracer element is then provided to the article producer. The article producer is then allowed to begin to convert the raw material to a finished article using the fabrication equipment. The raw material is analyzed for the presence of the tracer element while the fabrication equipment is operated. Appropriate action, such as charging a royalty or shutting down the fabrication equipment, is then taken in the event the tracer element is not detected.

12 Claims, No Drawings

LINKING ON-LINE ANALYSIS AND TRACER TECHNOLOGY

FIELD OF THE INVENTION

The present invention relates to a method of providing equipment or technology for use with raw materials. The method provides a way to determine whether such equipment is being used with raw material obtained from a pre-identified source.

BACKGROUND AND SUMMARY OF THE INVENTION

Suppliers of resin, or intermediate articles made from resin, often promote the use of their materials by providing manufacturing equipment. For example, a film supplier may provide and end-user with equipment used to convert film to a pouch or other package. This equipment and related technology may be provided at no cost, or at a reduced royalty rate, for so long as the end-user purchases all of its raw materials (film in this example) from the supplier who provided the equipment. Additionally, for quality control reasons, the seller of a particular piece of manufacturing technology may specify a particular source of raw material. Currently, however, there is no reliable way to ensure that the end-user is using only raw materials obtained from the supplier that provided the fabrication equipment, or providing accurate information as to how much alternatively-sourced raw materials are being used, or ensuring that only approved raw materials have been used with the equipment.

Technology now exists to allow resin manufacturers to add minor amounts of a unique material, sometimes referred to as a tracer element, to a resin. The tracer element is chosen so that it does not interfere with the performance of the resin, but can be detected using routine analysis. Such technology includes the FINGERPRINT™ Resins available from The Dow Chemical Company. Such modified resins are currently used to enable the resin manufacturer to evaluate and improve quality and consistency of the resins when used in applications not in the resin manufacturer's control. Thus, for example, Dow can get performance data on its resins by obtaining samples of pipe in actual use, if that pipe contains the tracer element which is unique to Dow.

The present invention involves a new use for this existing tracer element technology. The present applicant has found that the tracer technology can also be used to ensure that raw materials used with a piece of fabrication equipment come from an approved source, or at least monitor and report the amounts of alternatively-sourced raw material. The method involves the step of including an on-line analyzer with the equipment. The on-line analyzer will be capable of detecting a tracer element which can be included in the raw material being supplied for use with the equipment. If the tracer element is not detected in the raw materials being used with the fabrication equipment, then the fabrication equipment can be programmed to shut down. Alternatively, the fabrication equipment can be programmed to record the amounts of material processed which did not include the tracer element. In this way an accurate record of how much alternatively-sourced material is being used can be obtained, and appropriate royalties can be collected.

This technology can conceivably be used in multiple steps of a process to make an article of commerce. A tracer element can be added to the resin itself as part of the polymerization reaction or shortly afterwards as part of the pellitization process. Film, fiber, sheets or finished articles made from that resin will then also contain the tracer element. Alternatively the tracer element may be able to be added at later stages such as in film or fiber production.

DETAILED DESCRIPTION OF THE INVENTION

In one embodiment, the present invention is a method for ensuring that raw material used with a particular piece of fabrication equipment comes from an approved source. The method involves first providing fabrication equipment to a user of the raw material. The fabrication equipment will include an on-line analyzer for detecting the presence of a tracer element. The on-line analyzer will be in electronic communication with the fabrication equipment to safely shut down the equipment in the event that raw material which does not contain a specified tracer element in a specified amount is attempted to be used with the fabrication equipment. The details of the identity and characteristics of the tracer element should be provided only to those raw material suppliers who have demonstrated that their products meet the requisite quality control standards. Thus only raw materials which have been pre-approved by the equipment manufacturer will contain the specific tracer element in specific amount. Accordingly, only approved raw materials will be capable of being processed by the fabrication equipment.

The specifics of the fabrication equipment are not limited in the present invention. In theory any fabrication equipment which converts raw material into a different product can be used with the present invention. It should be understood that "raw material" includes resin itself, but also includes films, fibers, sheets, and articles of any kind which may be used in a piece of fabrication equipment to be converted to another product in some manner. This includes packaging units which are "converted" only in the sense of being converted from an empty package to a full package; that is, the empty package is converted in the sense of being filled and sealed.

In another embodiment, the present invention is a method for increasing sales of a raw material. Often the fabrication equipment represents a hurdle for manufacturers, often just due to expense, but occasionally because the equipment may be protected by intellectual property rights. Raw material suppliers may be in a position to license, sell or lease the equipment to overcome this barrier. The raw material supplier may even do this below the market rate, in exchange for the manufacturer's assurance that they will purchase raw material for use in the equipment from the raw material supplier who helped in providing the equipment. In such a case, the on-line analyzer will be in electronic communication with a means for recording the specific amounts of raw material used which does not contain the tracer element. This information can be used to allow the equipment supplier to charge royalties, or otherwise seek compensation for the cost of the equipment and/or technology.

The tracer element for use with the present invention can be any tracer material known in the art. In general the tracer element can be any chemical which can be detected by a non-destructive analytical method like spectroscopy (including techniques such as IR, NMR, x-ray, etc) and which is not commonly used as an additive for the polymers/applications. In other words, the tracer element should be distinguishable from other additives which may likely be included in a polymer formulation (for example, antioxidants etc.) but still sufficiently "hidden" so that potential counterfeiters can not easily identify the substance used as the tracer element and include it in their own polymer formulations in order to pass off their formulations as coming from the original source.

These tracer elements include materials of organic origin like polystyrene and polypropylene (depending on the raw material), and/or materials of inorganic origin like metal-complexes/metal salts. Metal complexes/salts of transition metals like Niobium (Nb), Tantalum (Ta) and Molybdenum (Mo) can be advantageously used for certain raw materials. Examples include: alkylidene complex of Nb and Ta, Niobium nitrate nano particles (superconductor), Niobium-2-ethylhexanoate (yellow liquid soluble to organic solvents), Niobium alcoholate clusters, and etoxi with metal (M[Nb(OEt)6]2 where M=Mg, Ca, Sr, Ba). Rare earth elements could be also used as tracers, like oxides of Yttrium, Ytterbium, Erbium, Neodymium or Europium.

Other commonly known tracers capable of being used in the present invention include nano-particles and/or commonly known biomarkers (pristane, phytane, steranes, triterpanes, porphyrin, etc)

The tracer material should not interfere with the intended use of the raw material. Thus for example, only tracer elements which are certified for use with food should be used in any raw material which is intended for use in packaging food products. The selection of the tracer element should also take into account the steps in the manufacturing process with the raw material is expected to undergo. For example if it is known that particular resin pellets will be spun into a fiber, then tracer element of very small particle size would be desired so as to not interfere with the spinning process. Similarly, if a particular resin will be compounded with other resin at high temperatures and pressures to ensure proper mixing, then the tracer element should be selected to ensure that it will not degrade at such temperatures or pressures.

It should also be understood that more than one tracer element can be added. Particularly if more than one raw material supplier is adding tracer elements to their products, a combination of two or more tracer elements may be desirable to provide unique identifiers.

Depending on the choice of tracer element(s) and the sensitivity of the on-line detectors provided, the amounts of the tracer elements can also be varied to provide a unique identifier. With the ability to choose multiple tracer elements and the ability to vary the amount of each element, a nearly infinite number of different arrays can be used to identify the source of the product.

Similarly, the on-line analyzer can be chosen from among any of those commercially known to be capable of detecting the tracer element (or elements) selected to include in the source of the raw material. These include chemical analysis, electro-magnetic techniques, NMR or photochemistry/optical analysis, on-line gas chromatography and spectroscopy.

For purposes of this invention, "on-line" analyzers include analyzers which are analyzing material as it is proceeds along the manufacturing process, as well as analyzers which remove small amounts of material from the manufacturing process for analysis. These latter types of analyzers are sometimes referred to as "at-line" detectors.

What is claimed is:

1. A method of obtaining value from providing fabrication equipment comprising the steps of
   a. providing fabrication equipment to an article producer, which equipment includes an on-line analyzer for detecting the presence of a tracer element;
   b. providing raw material containing the tracer element to the article producer, wherein the raw material is resin, fiber, film, molded articles, or sheet;
   c. allowing the article producer to convert the raw material to a finished article using the fabrication equipment;
   d. analyzing the raw material for the presence of the tracer element using the on-line analyzer;
   e. if the tracer element is not present, recording the volumes of resin, fiber, film, molded articles, or sheet used.

2. The method of claim 1 wherein the tracer element comprises a material of inorganic origin.

3. The method of claim 2 wherein the material of inorganic origin comprises a metal complex and/or metal salt.

4. The method of claim 1 further comprising shutting down the fabrication equipment in the event the tracer element is not detected.

5. The method of claim 1 further comprising the step of charging a royalty based on the recorded volumes.

6. The method of claim 1 including a further step of charging the article producer a royalty based on the volumes of resin, fiber, film, molded articles or sheet used which did not contain the tracer element.

7. The method of claim 1 wherein the raw material comprises a polyolefin resin.

8. The method of claim 1 wherein the on-line analyzer detects the amount of the tracer element in addition to the presence, and wherein action taken in step e. is based on whether or not the tracer element is present in the proper amount.

9. The method of claim 1 wherein more than one tracer element is added to the raw material and where the analyzer detects the presence and/or amount of each tracer element added.

10. The method of claim 1 wherein the tracer element comprises a material of organic origin.

11. The method of claim 1 wherein more than one tracer element is added and wherein the amount of each tracer element is varied to provide a unique identifier.

12. A method for ensuring that raw material used with a particular piece of fabrication equipment is of adequate quality comprising the steps of
   a. providing fabrication equipment to an article producer, which equipment includes an on-line analyzer for detecting the presence of a tracer element;
   b. identifying raw material producers whose raw materials meet desired standards;
   c. providing the identity and optionally ranges of amounts of one or more tracer elements to the identified raw material producer;
   d. allowing the article producer to convert the raw material to a finished article using the fabrication equipment;
   e. analyzing the raw material for the presence and optionally the amount of the one or more tracer elements provided to the identified raw material producer using the on-line analyzer; and
   f. communicating a signal to safely shut down the fabrication equipment in the event the presence and optionally the amount of the one or more tracer elements is not detected in the raw material.

* * * * *